United States Patent [19]

Christenson et al.

[11] Patent Number: 5,024,847

[45] Date of Patent: Jun. 18, 1991

[54] SULFUR CONTAINING ACYCLIC TERPENES

[75] Inventors: Philip A. Christenson, Midland Park, N.J.; Robert G. Eilerman, Merrick, N.Y.; Paul J. Riker, Lodi; Brian J. Drake, Clifton, both of N.J.

[73] Assignee: BASF K&F Corporation, Whippany, N.J.

[21] Appl. No.: 408,620

[22] Filed: Sep. 18, 1989

[51] Int. Cl.$^5$ ................................................. A23L 2/26
[52] U.S. Cl. ...................................... 426/535; 568/59; 568/69
[58] Field of Search .................. 426/534, 535; 568/38, 568/61, 579, 59, 873, 69; 558/230; 562/205

[56] References Cited

U.S. PATENT DOCUMENTS

Re. 30,363  8/1980  Kratz et al. .......................... 426/534
4,131,687 12/1978  Mussinan et al. ..................... 568/579

FOREIGN PATENT DOCUMENTS 0073984  3/1983  European Pat. Off. ............ 426/534

OTHER PUBLICATIONS

Infrared Spectra of Monoterpenes and Related Compounds. II. Terpene Alcohols, by Mitzner et al., Applied Spectroscopy, vol. 22, No. 1, 1968.

*Primary Examiner*—Donald E. Czaja
*Assistant Examiner*—Tony Weier

[57] ABSTRACT

This invention provides oxygen or sulfur containing compounds possessing fruity, floral, or woody odors. These compounds may be used to fragrance or flavor a variety of consumer products such as tobacco products, foodstuffs, beverages, gums, mouthwashes, toothpastes, cosmetics, pharmaceutical preparations, and medicinal products. The disclosure also provides a process for the preparation of these compounds.

8 Claims, No Drawings

SULFUR CONTAINING ACYCLIC TERPENES

FIELD OF THE INVENTION

This invention relates to novel oxygen or sulfur containing compounds useful in fragrance and flavor compositions. The invention also includes a novel process for preparing these compounds as well as fragrance and flavor compositions containing these compounds.

BACKGROUND OF THE INvENTION

Artificial fragrance and flavoring ingredients have long been used to enhance, improve, or modify the aroma or flavor in perfume compositions, pharmaceutical and medicinal products, and a wide variety of foodstuffs and consumable materials. Artificial fragrance and flavoring ingredients have numerous and significant advantages over natural ingredients, such as uniformity of aroma and flavor and decreased tendency to spoil during storage. Accordingly, close reproduction of floral, fruit-like and vegetable aromas and flavors has been the subject of long and continuous searches and efforts.

Research in this area has lead to the development of a number of oxygen and sulfur containing compounds which have desirable aroma and flavor characteristics. For example, the use of 3,7-dimethyl-octa-2,6-dienyl mercaptan as an odorant and flavorant has been described in U.S. Pat. Nos. 3,896,175 and 3,996,387. This compound possesses an aroma which smells like berry and grapefruit.

British Patent No. 1,546,283 describes the cyclogeranyl mercaptan possessing a grapefruit-like odor.

U.S. Pat. No. 4,600,576 relates to dimethyl octadienyl mercapto esters as food flavorants which have grapefruit and citrus-like flavor characteristics.

European Patent 0054847 A2 describes certain cyclic terpenes which are thiol substituted and used to flavor certain foods.

Morrison, "Synthesis of 4-and 5-Benzothiazol-2-yldithio-2,6-dimethylocta-2,6-diene and Other Models for Pendent Groups in the Sulfur Vulcanization of Natural Rubber", J. Chem. Soc. Perkin Trans. I pp. 101 to 106 (1984) describes certain thioacetates, thiols and related compounds used for the sulfur vulcanization of natural rubber. No reference is made to usefulness in perfumes or flavors as organoleptic agents.

Gauthier et al., "A Mild and Efficient Synthesis of Thiolesters from Alcohols", Tet. Lett. Vol. 27, No. 1, pp. 15 to 18 (1986) relates to the synthesis of numerous thioesters without addressing an ultimate utility for the compounds.

Volante, "A New, Highly Efficient Method for the Conversion of Alcohols to Thiolesters and Thiols", Tett. Let. Vol. 22, No. 33, pp. 3119 to 3122 (1981) describes the conversion of alcohols to thiols and thioesters at the three position in 3B cholesteryl compounds.

U.S. Pat. No. 2,993,857 relates to certain cyclic thiol substituted terpenes having organoleptic properties.

U.S. Pat. No. 4,478,865 describes sulfur containing cycloterpenes which possess organoleptic properties of a fruity, especially grapefruit, character. Research pertaining to these compounds is also described in E. Demole et al., "176.1-p-Menthene-8-thiol: A Powerful Flavor Impact Constituent of Grapefruit Juice (Citrus paradisi MacFayden)", Helv. Chim. Acta, 65:1785–1794 (1982).

The use of 1,3-oxathiane and 1,3-oxathiolane derivatives as perfuming and flavoring agents has been described in U.S. Pat. Nos. 4,220,561 and 4,262,030.

The isolation and identification of several sulfur containing compounds which possess passionfruit-like and grapefruit-like organoleptic properties is described in W. Pickenhagen and E. Demole, Natural Trace Sulfur Compounds and their Contribution to Fruit Flavors, IXth International Congress of Essential Oils, Singapore (Book #3 p. 1–7) March, 1983.

In their pure state, many of the above compounds, especially the sulfur containing compounds, have very powerful and unpleasant odors. Examples of sulfur containing materials which are malodorants are t-butylthiol or mercaptoacetic acid. Accordingly, due to the fact that the chemical mechanisms of odor perception are currently not well understood, reproduction of certain fruit-like and floral odors is difficult and unpredictable. Thus, materials which will closely simulate such odors are highly desirable.

The availability of such artificial ingredients is expected to render alternative food sources, such as processed foods and non-meat sources of protein, more attractive and palatable, by improving the flavors and aromas. Thus, chemical compounds which closely imitate or reproduce the aromas and flavors of a variety of tropical and citrus fruits and floral odors are highly desirable.

One object of the present invention is to develop novel compounds possessing fruity or floral odors.

Another object of the present invention is to develop a process for synthesizing sulfur containing hydrocarbon compounds which possesses useful organoleptic properties.

Yet another object of the present invention is to provide oxygen and sulfur containing compounds for use as fragrance and flavoring ingredients. These compounds can enhance, improve, alter, or modify the fragrance properties of perfumes and perfumed articles, and the flavor properties of foodstuffs, beverages, gums, mouthwashes, toothpastes, pharmaceutical preparations, medicinal products, and tobacco or tobacco products by adding thereto an effective amount of the above formula.

SUMMARY OF THE INvENTION

This invention includes compounds represented by structured formula I:

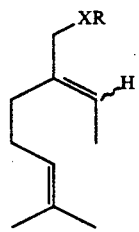

wherein
X represents an oxygen or sulfur atom;
R represents H, lower alkyl or an acyl group containing 1 to 3 carbon atoms, and ~H indicates an E or Z double bond configuration.

DETAILED DESCRIPTION OF THE INVENTION

In accordance with the above-mentioned objects and others, the following invention is directed to compounds possessing fruity, floral, or woody odors represented by structural formula I:

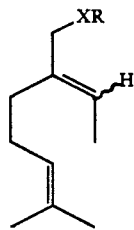

wherein X represents an oxygen or sulfur atom; R is hydrogen, lower alkyl, or an acyl group containing 1 to 3 carbons; and ∼H indicates an E or Z double bond configuration.

Essentially pure E or Z isomers as well as mixtures thereof are included herein.

This invention also includes a perfume composition which contains an effective amount of the compounds of formula I in combination with an acceptable carrier.

The invention also provides a flavoring composition which contains an effective amount of a compound of formula I in combination with an acceptable carrier. The flavor composition may be included in various foods, e.g., ice cream, yogurt, candy, etc. or beverages, e.g., fruit juice, to provide or enhance the floral, tropical fruit, fruity or mango-like aroma or taste contained therein. A novel process for the preparation of compounds of the above formula is also provided.

The present invention provides oxygen or sulfur containing acyclic terpenes useful for augmenting or enhancing the flavor of consumable materials. These consumable materials include foodstuffs, beverages, gums, mouthwashes, toothpastes, medicinal products, pharmaceutical products, and tobacco or tobacco products. These compounds are also useful in perfume compositions, colognes, and perfumed articles to alter, modify, or enhance fragrance compositions or articles.

As used herein the term "organoleptic" refers to compounds of the invention which stimulate the sense of smell or taste, and are thus perceived as having a characteristic odor and/or flavor.

The terms "odor", "fragrance" and "smell" are used interchangeably whenever a compound is referred to as an organoleptic which is intended to stimulate the sense of smell.

The terms "flavor", "flavoring" and "flavorant" are also used interchangeably whenever an organoleptic compound is referred to which is intended to stimulate the sense of taste.

The following chemical terms are used throughout the specification, and are defined as follows unless otherwise indicated:

Alkyl - branched or unbranched saturated carbon chain containing 1 to 12 carbon atoms, with lower alkyl representing a chain containing 1 to 6 carbon atoms.

Acyl - an organic radical derived from an organic acid by the removal of the hydroxyl group.

The compounds of the present invention may be used as organoleptics in consumable materials and in nonconsumable compositions. Additionally, these compounds may be used as enhancing or co-active agents in conjunction with at least one other organoleptic agent.

Fragrance compositions containing the compounds of the invention and at least one other organoleptic agent include various perfumed articles such as soaps, detergents, air fresheners, deodorants, fabric softeners, colognes, and other products.

Illustrative examples of compounds falling within the scope of this invention and descriptions of their organoleptic properties are presented below in Table I.

TABLE I

| Compound Structure | Name | Organoleptic Description |
|---|---|---|
| SH | 2-ethylidene-6-methyl-5-hepten-1 thiol | A strong, sulfur odor which becomes tropical fruit or mango-like at high diltuion. |
| SCOCH₃ | 2-ethylidene-6-methyl-5-hepten-1-thiol acetate | A strong, sulfur or rubber type odor which becaomes fruity, with a citrus-like note at high dilution. |
| OH | 2-ethylidene-6-methyl-5-hepten-1-ol | A floral odor with woody note. |
| 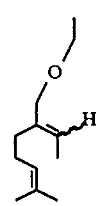 | 2-ethylidene-6-methyl-5-hepten-1-yl ethyl ether | anisic-like odor with citrus-like and floral undertones. |

The oxygen or sulfur containing terpenes of the present invention may be prepared from the corresponding keto esters 7-methyl-3-carboalkoxy-6-octen-2-one by following Scheme I.

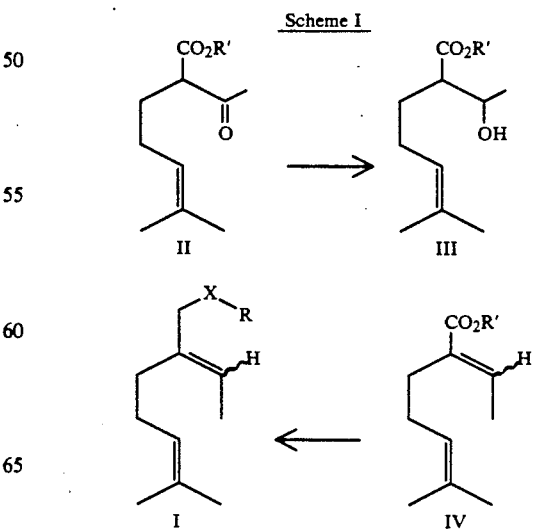

Scheme I

Keto ester II may be prepared as described by Cl. Daessle, H. Favre, and H. Schinz in *Helv. Chim. Acta*, 40:2278 (1957). Keto ester II may be conveniently reduced to alkyl 2-(4-methyl-3-pentenyl)-3-hydroxybutyrate III (wherein R' is lower alkyl) by contact with a metal hydride reducing agent. See e.g., Chapter 2 of H.O. House, "Modern Synthetic Reactions", (2nd ed. W.A. Benjamin, Inc., Menlo Park, CA 1972). Generally, alkali borohydrides, sodium cyanoborohydride, and sodium bis(2-methoxyethoxy)aluminum hydride are preferred, with the borohydrides being most preferred.

A wide range of solvents and reaction temperatures may be used in the reaction. Solvents which may be used in the process include methanol, ethanol, isopropanol and water, toluene, and tetrahydrofuran. The preferred solvent is dependent upon the reducing agent used. Accordingly, once the reducing agent is specified, the preferred solvent will be apparent to those skilled in the art. The process of Scheme I may be conducted in the temperature range of about −10° C. to 80° C., the preferred temperature range being −10° C. to 60° C., and the most preferred temperature range being −10° C. to 10° C.

The choice of solvent and reaction temperature is dependent upon the metal hydride employed. Sodium borohydride in a lower alkanol (such as methanol, ethanol, or isopropanol) in a temperature range of −10° C. to 25° C. is the most preferred reaction condition.

Other methods of converting keto ester II to an alcohol III are available. See, for example, C.A. Buehler and D.E. Pearson, "Survey of Organic Synthesis", 1:200–204 (1970) and 2:228–237 (1977).

Alcohol III may be dehydrated to produce the diene IV. This dehydration may be achieved by a variety of means, e.g., C.A. Buehler and D.E. Pearson, "Survey of Organic Synthesis", 1:71–75, 85–88 (1970) and 2:80–83, 92–95 (1977). The hydroxyl group in alcohol III may be converted to an intermediate leaving group including the acetate, methanesulfonate, p-toluenesulfonate or halide. The intermediate compound is typically not isolated, but rather converted directly to diene IV upon treatment with base. Preferred reagents for this conversion include acetic anhydride, methanesulfonyl chloride, p-toluenesulfonyl chloride and napthalenesulfonyl chloride. The more preferred reagents are acetic anhydride and methane sulfonyl chloride, and the most preferred reagent is acetic anhydride.

Preferred bases for this dehydration reaction include pyridine, triethylamine, dimethylaminopyridine, quinoline, 1,8-diazabicyclo[5.4.0]undec-7-ene, 1,5diazabicyclo[4.3.0]non-5-ene, ethyldiisopropylamine, 1,4diazabicyclo[2.2.2]octane, and mixtures of the above. The more preferred bases are pyridine, triethylamine, dimethylaminopyridine, 1,8-diazabicyclo[5.4.0]undec-7-ene, 1,5-diazabicyclo[4.3.0]non-5-ene and combinations of the above. The most preferred bases are dimethylaminopyridine, 1,8diazabicyclo[5.4.0]undec-7-ene and a mixture of the two bases.

Inert solvents useful for the dehydration reaction include benzene, toluene, xylene, hexane, tetrahydrofuran, dimethoxyethane, dioxane, or dichloroethane. The more preferred solvents are benzene, toluene, and xylene, and the most preferred solvent is toluene. The dehydration reaction may be conducted in the temperature range of about 80° C. to 175° C., the more preferred temperature range being 80° to 160° C. and the most preferred range being 90° C. to 160° C.

Diene IV may be reduced to the alcohol I(X=O, R=H) with various metal hydrides. The preferred metal hydrides are aluminum hydride, lithium aluminum hydride, sodium bis(2-methoxyethoxy) aluminum hydride, and diisobutyl aluminum hydride. The more preferred reagents are lithium aluminum hydride and diisobutyl aluminum hydride with the most preferred reagent being dissobutyl aluminum hydride.

Appropriate solvents include ether, tetrahydrofuran, dimethoxyethane, hexane, benzene, toluene, and dichloromethane. The reaction may be performed at a temperature range of −100° C. to 60° C. The preferred temperature range is −90° C. to 40° C., and the most preferred temperature range is −78° C. to 30° C.

Alcohol III (X=O, R=H) may thereafter be converted to derivative I (X=O, R=lower alkyl or an acyl group of 1–3 carbon atoms) by alkylation or acylation under standard conditions, such as are described in C. A. Buehler and D. E. Pearson, "Survey of Organic Synthesis", 1:296–305, 802–818 (1970) and 2:301–319, 715–724 (1977).

Alcohol I may also be converted to a thiol by various methods. For example, see "Thiols" by G.C. Barrett in Vol. 3, *Comprehensive Organic Chemistry*, p. 6–12, (D.H.R. Barton and W.D. Ollis eds., Pergamon Press, 1979) and "Chapter 4: The Preparation of Thiols", J.L. Wardell *The Chemistry of the Thiol Group Part* 1, p. 163–269.

One thiol conversion method which is particularly useful involves conversion of the hydroxyl group of III (X=O, R=H) to an intermediate leaving group such as a halide, p-toluene-sulfonate or methanesulfonate, followed by treatment with sodium sulfide, sodium thioacetate, or a related sulfur-containing reagent. Another conversion method involves treating the alcohol with thioacetic acid and a Lewis acid such as zinc iodide to produce the thioacetate I (X=S, R=COCH$_3$) see e.g., J.X. Gauthier, Tetrahedron Lett., 27: 15–18 (1986).

Thiols may also be produced by treating alcohols with a mixture of thioacetic acid, triphenylphosphine, and diisopropyl azodicarboxylate followed by hydrolysis or reduction of the resulting thiol acetate. See, N.J. Morrison, J. Chem. Soc., Perkin Trans I, p. 101–106 (1984), and R.P. Volante, Tetrahedron Lett., (1981) 22: 3119–3122.

Thioalkanoates I (X=S, R=acyl group of 1–3 carbon atoms) may be produced by treating an alcohol III (X=O, R=H) with a triarylphosphine, a lower dialkyl azodicarboxylate and a thioalkanoic acid of 1–3 carbon atoms in an inert solvent. Triphenylphosphine and tri(p-methylphenyl)phosphine are preferred, and triphenylphosphine is the most preferred. The preferred azodicarboxylates are methyl, ethyl, isopropyl, and butyl esters. Diethyl and diisopropyl azodicarboxylates are most preferred.

Ether, tetrahydrofuran, dioxane, dimethoxyethane, or t-butyl methyl ether may be used as a solvent for the thioalkanoate reaction. Ether, tetrahydrofuran, or dimethoxyethane are more preferred, and the most preferred solvent is ether or tetrahydrofuran.

The reaction may be conducted in the temperature range of about −20° C. to 40° C. The more preferred temperature range is −10° C. to 30° C., and 0° C. to 25° C. is the most preferred range.

Thiol I (X=S, R=H) may be produced from thioalkanoates I (X=S, R=an acyl group of 1–3 carbons) by hydrolysis or reduction. Hydrolysis entails treatment of the thioalkanoate with a metal hydroxide or carbonate and water in a protic solvent. Group I or Group II metal hydroxides may be employed in the hydrolysis reaction, with lithium, sodium, potassium, calcium, barium, and magnesium hydroxides and carbonates being preferred reagents. Lithium, sodium, potassium, and barium carbonates or hydroxides are more preferred, and the most preferred reagents are sodium and potassium carbonates and hydroxides.

Various lower alkanols combined with water may be used as reagents. Methanol, ethanol, isopropanol and t-butanol with water are the more preferred solvents, and the most preferred solvents are methanol and ethanol mixed with water. The reaction may be performed at a temperature ranging from about −10° C. to about 80° C. The more preferred range is 0° C. to 70° C., and the most preferred range is from 25° C. to 65° C.

Alternatively, thioalkanoates may be converted to the thiol I (X=S, R=H) by reduction with a metal hydride reducing agent such as lithium aluminum hydride, aluminum hydride, sodium bis(2-methoxyethoxy)aluminum hydride, or diisobutyl aluminum hydride. The more preferred reducing agents are lithium aluminum hydride, sodium bis(2-methoxyethoxy)aluminum hydride, and diisobutyl aluminum hydride, and the most preferred reducing agent is lithium aluminum hydride. The selection of solvent and reaction temperature is dependent upon the reducing agent used. Ether, tetrahydrofuran, dioxane, or dimethoxyethane are the preferred solvents for lithium aluminum hydride. The more preferred solvents are ether, tetrahydrofuran and dimethoxyethane; ether and tetrahydrofuran are the most preferred solvents.

The preferred temperature range for reducing the thiolakanoate to the thiol in the presence of lithium aluminum hydride is from about 0° C. to about 80° C. The more preferred range is from 0° C. to 65° C. and the most preferred range is from 0° C. to 40° C.

Thiol I (X=S, R=H) may be readily converted to the thioalkyl compounds I (X=S, R=lower alkyl) by treatment with the appropriate alkylating reagents.

The compounds of formula I may exist as the E isomer or the Z isomer. Both the E and the Z isomers are included in the present invention in pure form and in admixture.

The compounds of the invention possess organoleptic properties and are therefore useful in flavor and fragrance compositions. These compounds may be used singly in an amount effective to impart a characteristic flavor or fragrance to a material. More commonly, however, the compounds are mixed with other flavor or fragrance components in an amount sufficient to provide the desired flavor or fragrance characteristic. The amount required to produce the desired, overall effect varies depending upon the particular compound chosen, the product in which it will be used, and the particular effect desired. For example an effective amount of the compound may vary from about 0.005 ppm to about 500 ppm. More commonly, the compounds of the invention are used in the preferred range of about 0.01 ppm to about 10 ppm.

The compounds may be admixed with various solvents, carriers, gums, emulsifiers, and the like commonly used in the preparation of flavorings.

The flavor compositions obtained by mixing the compounds of the invention with other flavoring materials may be used to flavor foodstuffs, beverages, gums, mouthwashes, toothpastes, pharmaceutical preparations, medicinal products, and tobacco or tobacco products.

The compounds of the invention when used in perfume compositions alter, modify, or enhance the fragrance compositions or articles. The amount of the compounds used to produce an organoleptic effect may vary from 0.001% to 25% by weight. More commonly, the usage level ranges from 0.01% to 10% by weight. The compounds of the invention may be mixed with numerous ingredients generally contained in such preparations, e.g., diethylphthalate, ethanol, dipropylene glycol or other solvents, carriers and emulsifiers. Fragrance compositions containing the compounds of the invention and at least one other organoleptic agent may be used in various perfumed articles such as soaps, detergents, air fresheners, deodorants, fabric softeners, colognes, and other products.

The following examples are given to illustrate certain preferred embodiments of the invention. It is be understood that these examples are illustrative only, and the invention is not restricted thereto.

All parts, proportions, percentages, and ratios used herein are by weight unless otherwise indicated.

PREPARATIVE EXAMPLE 1

Ethyl 2-(4-Methyl-3-Pentenyl)-3-Hydroxybutyrate

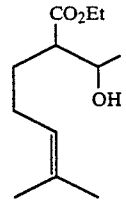

Sodium borohydride (22.9g, 0.605 mol) was added portionwise over a 1h period to a cold (0° C.) solution of 7-methyl-3-carboethoxy-6-octen-2-one (42.4g, 0.2 mol, which may be prepared as described by Cl. Daessle, H. Favre, and H. Schinz, *Helv. Chim. Acta,* 40:2278 (1957)) in ethanol (424 mL). The mixture was allowed to rise to 25° C. over a 0.5h period. After the mixture was stirred at 25° C. for 3.5h, acetone (50 mL) was added dropwise over a 15 min period. After stirring the mixture for 15 min, 25% aqueous acetic acid (200 mL) was added cautiously. The mixture was concentrated under reduced pressure to about 250 mL. The residue was diluted with water (150 mL) and extracted with methylene chloride (3×250 mL). The extracts were washed with water (2×100 mL) brine (100 mL) and dried over sodium sulfate. Evaporation of solvent produced 45.4g of crude product. A sample of the crude was kugelrohr distilled (0.5 mm, 150° C. bath temp.) to provide a sample for analysis of ethyl 2-(4-methyl-3-pentenyl)-3-hydroxybutyrate 2(GLC purity: two isomers; 50.9% and 43.1%). NMR (CDCl$_3$, 60 MHz) δ 1.2 (3H, d, J=7Hz), 1.23 (3H, t, J=7Hz), 1.58 (3H, s), 1.67 (3H, s), 1.0–2.8 (5H, m), 3.6–4.1 (1H, m), 4.17 (2H, q, J=7Hz), 4.9–5.3 (1H, m); IR (film) ν$_{max}$ 330, 2960, 2910, 30, 1450 cm$^{-1}$; MS m/e 214, 199, 181, 143, 99, 82. Both isomers display similar mass spectra. The abbreviation Et as used herein represents —CH$_2$CH$_3$.

PREPARATIVE EXAMPLE 2

Ethyl 2-Ethylidene-6-Methyl-5-Heptenoate (E,Z)

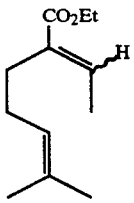

A mixture of ethyl 2-(4-methyl-3-pentenyl)-3-hydroxybutyrate (23.0g, 0.107 mol), acetic anhydride (14.28g, 0.14 mol), dimethylaminopyridine (0.714g, 0.0058 mol), 1,8diazabicyclo[5.4.0]undec-7-ene (42.5g, 0.28 mol) and toluene (250 mL) was heated in a stainless steel autoclave at 110° C. for 4h and then at 150° C. for 6h. The mixture was cooled, washed sequentially with water (50 mL), 2N HCl (3×50 mL), sodium bicarbonate solution until neutral, and dried (sodium sulfate). The solvent was evaporated and the residue distilled to provide 9.93g of ethyl 2-ethylidene-6-methyl-5-heptenoate (GLC purity 94%, about an 8:1 mixture of E:Z isomers). NMR (CDCl$_3$60 MHz) δ 1.28 (3H, t, J=7Hz, 1.62 (3H, s), 1.68 (3H, s), 1.80 (3H, d, J=7Hz), 1.6–2.4 (4H, m), 4.21 (2H, q, J=7Hz), 4.9–5.3 (1H, m), 6.87 (1H, q, J=7Hz), IR 2960, 2910, 1715, 1640, 440, 1370, 1270 cm$^{-1}$; MS m/e 196, 167, 150, 69.

EXAMPLE 3

2-Ethylidene-6-Methyl-5-Hepten-1-ol(E,Z)

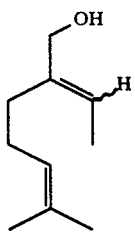

Diisobutyl aluminum hydride (22.4 mL of a 1M methylene chloride solution) was added dropwise over a 0.5h period to a cold (−78° C.) solution of ethyl 2-ethylidene-6-methyl-5-heptenoate (2.00g, 0.0102 mol) in methylene chloride (20 mL). The cooling bath was removed and the mixture was stirred at 25° C. for 4h. The reaction mixture was added to a 2:1 mixture of ice and 6N hydrochloric acid (30 mL). The aqueous layer was extracted with methylene chloride (3×15 mL). The extracts were washed sequentially with 2N hydrochloric acid (20 mL), sodium bicarbonate solution (until neutral), brine and dried (sodium sulfate). Evaporation of solvents provided 1.48g of crude product. Chromatography and kugelrohr distillation (bath temp: 90° C., 0.2 mm) provided 1.25g of 2-ethylidene-6-methyl5-hepten-1-ol (GLC purity: 98.5%; the E and Z isomers were not separated). NMR (250 MHz, CDCl$_3$) δ 1.60 and 1.68 (6H,2s), 1.64 (3H, d, J=7Hz), 2.00 (1H, broad s), 2.10 (4H, broad s), 4.01 and 4.14 (2H, 2s, ratio; 85:15; 4.01 peak assigned to E isomer), 5.14 (1H, m), 5.40 and 5.51 (1H, 2q, J=7Hz); IR (film) v$_{max}$ 3300, 2930, 1440, 1370 cm$^{-1}$; MS m/e 154, 139, 121, 107, 93, 69, 41.

EXAMPLE 4

2-Ethylidene-6-Methyl-5-Hepten-1-Thiol Acetate(E,Z)

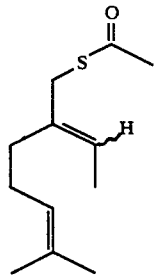

Diisopropyl azodicarboxylate (2.63g, 0.013 mol) was added dropwise over a 5 min period to a cold (0° C.) mixture of triphenylphosphine (3.40g, 0.013 mol) in tetrahydrofuran (20 mL). The mixture was stirred at 0° C. for 0.5h. A solution of thioacetic acid (0.99g, 0.013 mol) and 2-ethylidene-6-methyl5-hepten-1-ol (1.00g, 0.0065 mol) in tetrahydrofuran (20 mL) was then added dropwise over a 0.5h period to the cold (0° C.) reaction mixture. The mixture was stirred for 1h at 0° C. and then 1h at 25° C. The solvent was removed under reduced pressure. Hexane (40 mL) was added and the mixture was filtered to remove solids. Work-up, chromatography, and kugelrohr distillation (bath temp. 100° C., 0.5 mm) provided 1.15g of 2-ethylidene-6-methyl-5-hepten-1-thiol acetate (GLC purity 94.7%; isomers not separated). NMR (60 MHz, CDCl$_3$) δ 1.62 and 1.68 (6H, 2s), 1.63 (3H, d, J=6 Hz) 2.1 (4H, broad s), 3.57 (2H, broad s), 5.0–5.3 (1H, m), 5.49 (1H, q, J=6Hz); IR (film) v$_{max}$ 2920, 1685, 1430, 1125 940 cm$^{-1}$; MS m/e 212, 197, 169, 136, 69, 43.

EXAMPLE 5

2-Ethylidene-6-Methyl-5-Hepten-1-Thiol(E,Z)

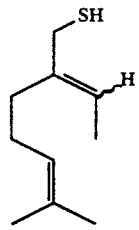

A solution of 2-ethylidene-6-methyl-5-thiol acetate (1.00g, 0.0047 mol) in ether (30 mL) was added over a 0.5h period to a cold (0° C.) mixture of lithium aluminum hydride (0.179g, 0.0047 mol) and ether (20 mL). The reaction mixture was then stirred at 25° C. for 2.5h. The mixture was cooled to −78° C. and ethyl acetate (2 mL) was added. After stirring the mixture for 10 min, 0.25N hydrochloric acid solution (20 mL) was added dropwise. The aqueous layer was extracted with ether (2×20 mL). The ether extracts were washed with water, sodium bicarbonate solution until neutral and dried (sodium sulfate). Evaporation of solvent and kugelrohr distillation (bath temp. 100° C., 0.5 mm) provided 0.75g of the title compound (GLC purity 90%; E and Z isomers not separated). NMR (250 MHz, CDCl$_3$) δ 1.38 (1H, t, J=7Hz), 1.61 and 1.69 (6H, 2 broad s), 1.66 (3H, d, J=7Hz), 2.05–2.40 (4H, m), 3.16 (2H, d, J=7Hz), 5.13 (1H, t, J=6Hz), 5.19 and 5.44 (2q, J=7Hz), ratio 15:85); IR (film) v$_{max}$ 3500 weak), 2970, 2920, 2850,

EXAMPLE 6

2-Ethylidene-6-Methyl-5-Hepten-1-yl Ethyl Ether(E,Z)

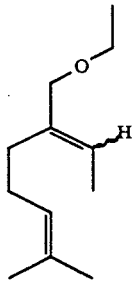

Sodium hydride (0.576g of a 50% oil-dispersion, 0.012 mol) was washed with tetrahydrofuran (2×10 mL). A solution of 2-ethylidene-6-methyl-5-hepten-1-ol (1.54g, 0.01 mol) in tetrahydrofuran (2 mL) was added dropwise to a suspension of the sodium hydride in tetrahydrofuran (10 mL) over a 10 min period. The mixture was stirred at 25° C. for 18h. Ethyl bromide (1 mL) was added and the mixture heated at 50° C. for 3h. The mixture was poured into water (10 ml) and extracted with hexane (4×20 mL). The extracts were washed with water (2×10 mL), brine (20 mL) and dried over sodium sulfate. Evaporation of solvents and chromatography of the residue provided after kugelrohr distillation (bath temp. 130°, 5 mm) 0.736g of 2-ethylidene-6-methyl-5-hepten-1-yl ethyl ether (GLC purity 91.4%; the E and Z isomers were not separated; NMR analysis indicates about an 8:1 mixture of E:Z isomers). NMR (CDCl$_3$, 250 MHz), δ 1.19 (3H, t, J=7 Hz), 1.61 (3H,s), 1.63 (3H,d,J=7 Hz), 1.68 (3H,s), 2.10 (4H, broad s), 3.42 (2H,q,J=7Hz), 3.86 and 3.98 (2H,2s,ratio,8:1), 5.20–5.08 (1H,m), 5.54–5.43 (1H,q,J=7Hz); IR (film) ν$_{max}$ 2960, 2910, 2850, 1440, 1375 cm$^{-1}$; MS m/e 182, 167, 136, 121, 113, 93, 69, 41.

EXAMPLE 7

Preparation of an Organoleptic Solution

A solution containing 0.1 ppm of 2-ethylidene-6-methyl5-hepten-1-thiol was prepared in water. The solution possessed a tropical fruit, mango-type flavor with a slight smoke-like note.

EXAMPLE 8

Preparation of an Organoleptic Composition

A standard sugar/acid/water solution was prepared by mixing 1.5 mL of a 50% citric acid solution and 98.5 mL of a high fructose corn syrup (76 brix) and diluting to 1000 mL. Addition of 2-ethylidene-6-methyl-5-hepten-1-thiol at a level of 0.25 ppm to the standard sugar/acid/water solution gave a composition which possessed a tropical fruity, mango-like flavor.

EXAMPLE 9

Preparation of an Organoleptic Composition

Addition of 2-ethylidene-6-methyl-5-hepten-1-thiol acetate at a level of 10 ppm to the standard sugar/acid/water solution gave a composition which possessed a fruity flavor with a citrus-like note.

EXAMPLE 10

Preparation of a Fruity Flavor Base

A sugar/acid/water solution was prepared by mixing 50% citric acid (1.5g), high fructose corn syrup, 76 brix (98.5g) and water (900g).

A fruity flavor base (labeled Ex 10-A for use below) was prepared by mixing the following ingredients:

| Ingredient | Weight (g) |
|---|---|
| Ethyl Butyrate FCC | 12.50 |
| Ethyl Acetate FCC | 10.00 |
| Hexyl Butyrate | 5.00 |
| cis-3-Hexenol | 0.75 |
| α-Decalactone | 0.50 |
| Novoviol B-Ionone Extra | 0.07 |
| Linalool FCC Synthetic | 0.50 |
| Allyl Caproate | 1.50 |
| Propylene Glycol FCC | 18.48 |
| Total | 49.30 |

To 4.93g of the fruity flavor base Ex 10-A was added 0.070g of 2-ethylidene-6-methyl-5-hepten-1-thiol (the compound produced in Example 5) to provide flavor sample Ex 10-B.

To 9.00g of the fruity flavor base Ex 10-A was added 1.00g of flavor Ex 10-B to provide flavor sample Ex 10-C.

To 9.90g of base Ex 10-A was added 0.10g of flavor Ex 10-B to provide flavor sample Ex 10-D.

A sample (0.05g) of each of the flavors Ex 10-A through Ex 10-D was mixed with 99.95g of the sugar/acid/water solution to provide a control sample, and 3 samples of 2-ethylidene-6-methyl-5-hepten-1-thiol containing the compound of Example 5 at different levels. Evaluation of the samples gave the results summarized below in Table II.

TABLE II

| Sample (in sugar/acid/water). | Conc. of the thiol (PPM) | Description |
|---|---|---|
| Ex 10-A | 0 | Fruity, apple-like taste |
| Ex 10-B | 7 | Very strong mango/tropical fruit-like flavor with a harsh sulfury note aftertaste. |
| Ex 10-C | 0.7 | A strong mango/tropical fruitlike flavor with a slight sulfury aftertaste. |
| Ex 10-D | 0.07 | A well-balanced mango/tropical fruit-like flavor with no perceptible aftertaste. |

EXAMPLE 11

Preparation of Fragrance Compositions

Two fragrance compositions were prepared: Red Rose A using geraniol and Red Rose B using 2-ethylidene-6-methyl-5-hepten-1-ol instead of geraniol. Each of the ingredients listed in Red Rose A and Red Rose B is a commercially available product, with the exceptions of 2-ethylidene-6-methyl-5-hepten-1-ol, which is be prepared as described in Example 3.

| Ingredient | Pts/wt. |
|---|---|
| Red Rose A | |
| Citral Quenched 507992 | 2.75 |

(Previous page continuation: 1650, 1440, 1370 cm$^{-1}$; MS m/e 170 (171, 172, 173), 155, 141, 127, 93, 81, 41.)

| Ingredient | Pts/wt. |
| --- | --- |
| Hydroxy Citronellal FCC Extra | 10.00 |
| Ionone Alpha White Coeur | 10.00 |
| Benzaldehyde FCC Rectified (10% DPG) | 10.00 |
| Iso Eugenol FCC | 14.00 |
| Phenylethyl Acetate FCC | 14.00 |
| Benzyl Acetate FCC Extra | 25.00 |
| Phenylethyl Alcohol FCC | 25.00 |
| Dipropylene Glycol | 49.25 |
| Citronellol FCC Extra 96% | 70.00 |
| Phenyl Acetaldehyde FCC (50% PEA) | 95.00 |
| Geranium Oil Algerian FCC Extra | 285.00 |
| Geraniol FCC 96-98% | 390.00 |
| Total | 1000.00 |
| Red Rose B | |
| Citral Quenched 507992 | 2.75 |
| Hydroxy Citronellal FCC Extra | 10.00 |
| Ionone Alpha White Coeur | 10.00 |
| Benzaldehyde FCC Rectified (10% DPG) | 10.00 |
| Iso Eugenol FCC | 14.00 |
| Phenylethyl Acetate FCC | 14.00 |
| Benzyl Acetate FCC Extra | 25.00 |
| Phenylethyl Alcohol FCC | 25.00 |
| Dipropylene Glycol | 49.25 |
| Citronellol FCC Extra 96% | 70.00 |
| Phenyl Acetaldehyde FCC (50% PEA) | 95.00 |
| Geranium Oil Algerian FCC Extra | 285.00 |
| 2-Ethylidene-6-methyl-5-hepten-1-ol | 390.00 |
| Total | 1000.00 |

Red Rose B possessed a more floral odor with citrus and woody undertones. The citrus note in B is less pronounced than in A.

Those of skill in the art will recognize that numerous variations and modifications from the specifics of the invention are possible from the teachings herein. Consequently, the scope of the invention is not limited to the specific embodiments described.

We claim:

1. A compound represented by the formula

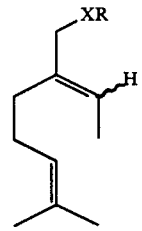

wherein
X is sulfur;
R is H, lower alkyl or an acyl group of 1 to 3 carbons; and
~H indicates the presence of an E or Z configuration.

2. A flavor composition comprising an organoleptically effective amount of a compound of claim 1 in combination with an organoleptically acceptable carrier.

3. The flavor composition according to claim 2 wherein the concentration of said compound is from about 0.005 ppm to about 500 ppm.

4. The flavor composition according to claim 3 wherein the compound is present in an amount ranging from about 0.01 ppm to about 10 ppm.

5. The flavor composition according to claim 4 wherein the concentration of said compound is 0.1 ppm.

6. A compound according to claim 1 wherein R represents hydrogen.

7. A compound having the name:
2-ethylidene-6-methyl-5-hepten-1thiol acetate, or
2-ethylidene-6-methyl-5-hepten-1thiol.

8. A method for flavoring a food comprising adding to said food a compound falling within the scope of one of claims 1, 6 and 7 in an amount effective for flavoring said food.

* * * * *